US005712261A

United States Patent [19]
Magnin et al.

[11] Patent Number: 5,712,261
[45] Date of Patent: *Jan. 27, 1998

[54] METHOD FOR PREVENTING OR TREATING HYPERTRIGLYCERIDEMIA

[76] Inventors: David R. Magnin, 40 Cottage Ct., Hamilton, N.J. 08690; Scott A. Biller, 31 Second St., Hopewell, N.J. 08525; John K. Dickson, Jr., 14 Shelter Rock Rd., Eastampton, N.J. 08060; R. Michael Lawrence, 48 W. Crown Ter., Yardley, Pa. 19067; Richard B. Sulsky, 71 Gregory La., Franklin Park, N.J. 08823

[*] Notice: The term of this patent shall not extend beyond the expiration date of Pat. No. 5,470,845.

[21] Appl. No.: 493,032

[22] Filed: Jun. 21, 1995

Related U.S. Application Data

[63] Continuation-in-part of Ser. No. 131,364, Oct. 4, 1993.

[51] Int. Cl.$^6$ ............................. C07F 9/38; A61K 31/66
[52] U.S. Cl. ................... 514/75; 514/39; 514/54; 514/89; 514/100; 514/102; 514/105; 514/107; 514/120; 514/121; 514/126; 514/129; 514/137; 514/310; 514/108
[58] Field of Search ............................. 514/105, 107, 514/108, 126, 102, 120, 121, 89, 100, 39, 54, 75, 129, 131, 310

[56] References Cited

U.S. PATENT DOCUMENTS

| | | |
|---|---|---|
| 4,871,721 | 10/1989 | Biller . |
| 5,025,003 | 6/1991 | Biller . |
| 5,102,907 | 4/1992 | Bergstrom et al. . |
| 5,157,027 | 10/1992 | Biller et al. . |
| 5,212,164 | 5/1993 | Biller et al. . |
| 5,470,845 | 11/1995 | Magnin et al. ............... 514/121 |

FOREIGN PATENT DOCUMENTS

| | | |
|---|---|---|
| 0494622A1 | 7/1992 | European Pat. Off. . |
| 0503520A1 | 9/1992 | European Pat. Off. . |
| WO9313096 | 12/1991 | WIPO . |
| WO9212156 | 1/1992 | WIPO . |
| WO9212157 | 1/1992 | WIPO . |
| WO9212158 | 1/1992 | WIPO . |
| WO9212159 | 1/1992 | WIPO . |

OTHER PUBLICATIONS

Hall, I. H. et al, "Hypolipidemic activity of boronated nucleosies and nucleotides in rodents", Biomed & Pharmacother (1993) 47, 79–87.

*Primary Examiner*—Herbert J. Lilling
*Attorney, Agent, or Firm*—Burton Rodney

[57] ABSTRACT

A method is provided for preventing and/or treating hypertriglyceridemia, and/or atherosclerosis and/or pancreatitis resulting from hypertriglyceridemia, employing a squalene synthetase inhibitor.

18 Claims, No Drawings

METHOD FOR PREVENTING OR TREATING HYPERTRIGLYCERIDEMIA

REFERENCE TO OTHER APPLICATIONS

This is a continuation-in-part of U.S. application Ser. No. 131,364 filed Oct. 4, 1993.

FIELD OF THE INVENTION

The present invention relates to a method for preventing, inhibiting and/or treating hypertriglyceridemia and/or atherosclerosis and/or pancreatitis resulting from hypertriglyceridemia by administering a therapeutic amount of a squalene synthetase (synthase) inhibitor.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds," Vol. I, Chapter 8, pp. 413–441, J. Wiley and Sons, 1981, and references therein). This enzyme is the first committed step of the de novo cholesterol biosynthetic pathway.

Squalene synthetase inhibitors which block the action of squalene synthetase (after the formation of farnesyl pyrophosphate) are disclosed in, for example, U.S. Pat. Nos. 4,871,721, 5,025,003, 5,157,027, 5,212,164, 5,254,544 and 5,332,728. The above patents disclose that the squalene synthetase inhibitors described inhibit de novo cholesterol biosynthesis and are useful in treating atherosclerosis, hyperlipemia, hyperlipidemia and/or hypercholesterolemia.

DESCRIPTION OF THE INVENTION

In accordance with the present invention, it has been found that hypertriglyceridemia and/or atherosclerosis and/or pancreatitis caused by hypertriglyceridemia may be prevented, inhibited and/or treated by administering a therapeutic amount of a squalene synthetase inhibitor including a prodrug ester thereof, which inhibits de novo cholesterol biosynthesis, and which does not contain boron or boron containing moieties.

Examples of squalene synthetase inhibitors suitable for use herein include bisphosphonate compounds disclosed in U.S. Pat. No. 5,157,027 to Biller et al which have the following structure

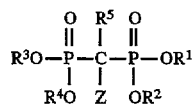

I including all stereoisomers thereof and pharmaceutically acceptable salts thereof, wherein $R^1$, $R^2$, $R^3$ and $R^4$ are the same or different and are H, alkyl, a metal ion or a prodrug ester;

$R^5$ is H, halogen or lower alkyl;

Z a lipophilic group containing at least 6 carbons and can be substituted alkenyl wherein the alkenyl group contains from 7 to 25 carbon atoms in the chain and from 1 to 4 double bonds; substituted alkynyl containing 1 to 4 triple bonds; mixed alkenyl-alkynyl containing 1 to 3 double bonds and 1 to 3 triple bonds and wherein alkenyl and/or alkynyl may be substituted or unsubstituted; or a substituted phenylalkyl group of the structure

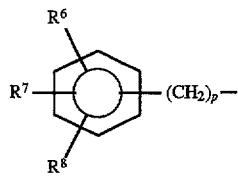

wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryloxy, hydroxy, halogen, nitro, amino, thiol, alkylthio, arylthio, alkyl-sulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino, at least one of $R^6$, $R^7$ and $R^8$ being alkenyl, alkenyloxy, alkynyl or alkynyloxy; and wherein the total number of carbons in the substituted phenylalkyl group exceeds 10 carbons.

The terms "substituted alkenyl" and "substituted alkynyl" as employed herein with respect to Z refers to alkenyl or alkynyl substituted with 1 to 4 groups which may be alkyl, alkenyl, alkynyl, halogen, hydroxy, alkoxy, alkenyloxy, alkynyloxy, aryl and/or cycloalkyl.

The $(CH_2)_p$ group may contain one or more alkyl, alkoxy, alkenyl, alkynyl, hydroxy and/or halogen substituents.

Preferred embodiments of formula I bisphosphonates have the structure

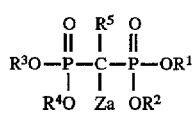

II wherein $R^1$, $R^2$, $R^3$, $R^4$ and $R^5$ are as defined above and Za is substituted alkenyl which includes from 1 to 4 double bonds and is substituted with from 1 to 4 alkyl groups.

In addition, other squalene synthetase inhibitors suitable for use herein are the bisphosphonates disclosed in U.S. Pat. No. 5,157,027 which have the structure

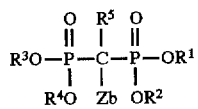

wherein Zb is

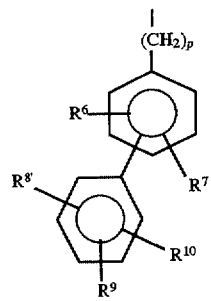

wherein $R^1, R^2, R^3, R^4, R^5, R^6, R^7$ and $(CH_2)_p$ are as defined hereinbefore, except that $R^6$ and $R^7$ may be any one of the groups included under the definition $R^6$ and $R^7$ set out hereinbefore without limitation; $R^8, R^9$ and $R^{10}$ are the same or different and are as defined hereinbefore with respect to $R^6$ and $R^7$, without limitation Preferred are compounds of formula III wherein the $R^{8'}$, $R^9$, $R^{10}$-substituted phenyl is para to the $R^6, R^7$-phenylene. These compounds have been found to inhibit cholesterol biosynthesis when administered orally.

In another embodiment of the present invention, bisphosphonate squalene synthetase inhibitors (disclosed in U.S. Pat. No. 5,157,027) may be employed which have the structure

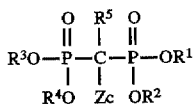   IV wherein $R^1, R^2, R^3, R^4$ and $R^5$ are as defined hereinbefore and Zc is alkyl wherein the alkyl group contains from 9 to 14 carbons in the normal chain and is substituted with 1, 2, 3 or 4 alkyl groups.

Still another embodiment of bisphosphonate squalene synthetase inhibitors (disclosed in U.S. Pat. No. 5,157,027) suitable for use herein have the structure

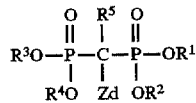   V wherein Zd is

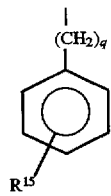

wherein $R^1, R^2, R^3, R^4$ and $R^5$ are as defined hereinbefore and $(CH_2)_q$ contains at least 2 carbons in the chain and may include 0, 1, 2 or 3 double bonds and/or 0, 1, 2 or 3 triple bonds in the normal chain, preferably 3 to 7 carbons in the normal chain, and may include one or more alkyl, alkenyl, alkynyl, alkoxy, hydroxy and/or halogen substituents; and $R^{15}$ is alkyl containing from 2 to 20 carbons, and preferably is in the para position, and the total number of carbons in Zd exceeds 10.

Other squalene synthetase inhibitors suitable for use herein are (phosphinylmethyl)phosphonate compounds disclosed in U.S. Pat. No. 5,212,164 to Biller et al and have the following structure

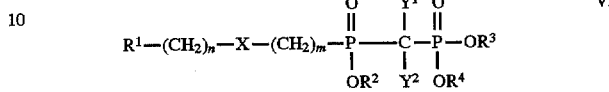   VI wherein m is 0, 1, 2 or 3; n is 0, 1, 2, 3 or 4; $Y^1$ and $Y^2$ are H or halogen, preferably H or F; $R^2$, $R^3$ and $R^4$ are independently H, metal ion, $C_1$ to $C_8$ alkyl or $C_3$ to $C_{12}$ alkenyl; X is O, NH, $$-\underset{\underset{R^{15}}{\overset{|}{CH_2}}}{\overset{|}{N}}-$$

or S (wherein $R^{15}$ is H or $C_1$ to $C_5$ alkyl); is $R^1$ is $R^5-Q^1-Q^2-Q^3-$ wherein $Q^1$, $Q^2$ and $Q^3$ are independently:

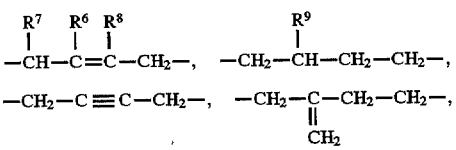

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl; $R^5$ is

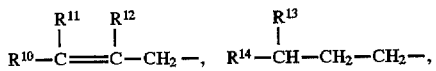

$R^{16}-C\equiv C-CH_2-$ (wherein $R^{16}$ is lower alkyl or H),

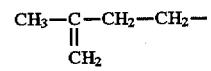

or $CH_3(CH_2)_p-$ where p is 2 to 7;

$R^{10}$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the provisos that if all of $Q^1$, $Q^2$ and $Q^3$ are bonds, then $R^{10}$ and $R^{11}$ cannot both be H, and $R^5$ cannot be $CH_3(CH_2)_p-$, with $p\leq 4$; if m is o, X is other than S; and if m is o and X is O, then n is 1, 2, 3 or 4, including all stereoisomers thereof and pharmaceutically acceptable salts thereof.

The term "lower alkenyl" or "alkenyl" as used above by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

Preferred are those compounds of formula VI which have the following formula:

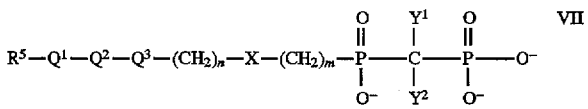  VII wherein $R^5$ is

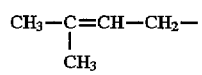

$Q^3$ is a bond;
$Q^2$ is

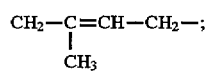

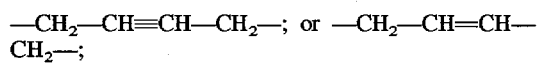

$Q^1$ is

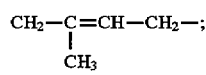

n is 0 or 1; m is 1 or 2; X is O and $Y^1$ and $Y^2$ are each H or F, in the form of the salts or acid.

In addition, preferred are those compounds of formula VI which have the following structure

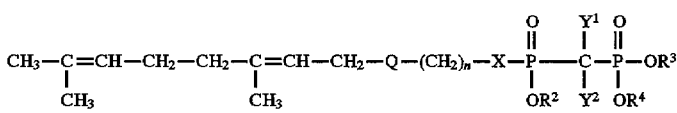  VIA-A wherein Q is

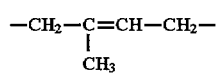

or a bond; n is 1 or 2; X is O, $Y^1$ and $Y^2$ are each H or each F; $R^2$, $R^3$ and $R^4$ are alkyl, H or metal ions; or X is NH and n is 0.

In addition, other squalene synthetase inhibitors which may be employed herein include phosphinylformic acids disclosed in U.S. Pat. No. 5,025,003 to Biller and have the following structure

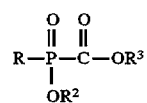  VIII wherein $R^2$ is a metal ion, lower alkyl or H;

$R^3$ is a metal ion or lower alkyl;

R is $R^1$—$(CH_2)_n$—, $R^1$—$(CH_2)_m$O— or $R^1$—$(CH_2)_m$OCH$_2$—, wherein n is 1 to 4, m is 0 to 3; and $R^1$ is $R^5$—$Q^1$—$Q^2$—$Q^3$— wherein $Q^1$, $Q^2$ and $Q^3$ are independently:

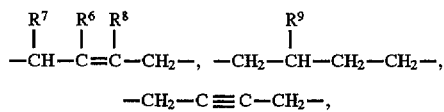

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, fluoro or fluoroalkyl (e.g., $CH_2F$, $CF_3$); $R^7$ is H, fluoro, lower alkyl or alkylthio; $R^8$ is H, fluoro, trimethylsilyl or lower alkyl; $R^9$ is H, or lower alkyl; $R^5$ is

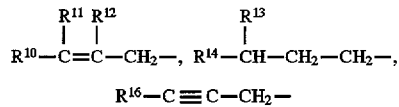

(wherein $R^{16}$ is lower alkyl or H), or $CH_3(CH_2)_p$— where p is 2 to 7; $R^{10}$ and $R^{11}$ are independently hydrogen, lower alkyl such as methyl or ethyl, fluoro, lower alkenyl or fluoroalkyl or $R^{10}$ and $R^{11}$ can be taken together to form $(CH_2)_s$, where s is 2 to 7; $R^{12}$ is hydrogen, lower alkyl, fluoro or lower alkenyl; $R^{13}$ and $R^{14}$ are independently lower alkyl such as methyl or ethyl; with the proviso that if all of $Q^1$, $Q^2$ and $Q^3$ are bonds, then $R^{10}$ and $R^{11}$ cannot both be H, and $R^5$ cannot be $CH_3(CH_2)_p$, with p<4, including all stereoisomers thereof and pharmaceutically acceptable salts thereof.

The term "lower alkenyl" or "alkenyl" as used herein is defined hereinbefore.

Preferred are those compounds of formula VIII wherein $R^1$ is

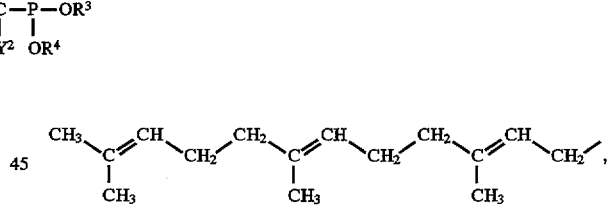

n is 1, 2 or 3, m is 1 or 2, $R^2$ is H or a metal ion, and $R^3$ is lower alkyl, a metal ion or H.

Other squalene synthetase inhibitors suitable for use herein include (phosphinylmethyl)phosphonates disclosed in U.S. Pat. No. 4,871,721 to Biller and have the following structure:

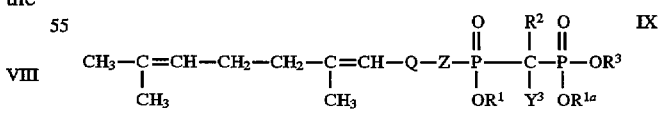  IX wherein Q is

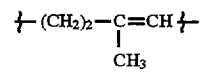

or a bond;

Z is —$(CH_2)_n$— or —$(CH_2)_p$—CH=CH—$(CH_2)_m$, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

Preferred are those compounds of formula IX which have the following structure

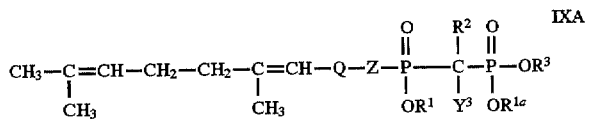

IXA wherein Q is

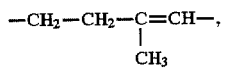

Z is —$CH_2CH_2$— or —CH=CH—; $R^2$ and $R^3$ are each H or each F; R, $R^1$ and $R^{1a}$ are OH or metal ions.

Another embodiment of squalene synthetase inhibitors which may be employed are hydroxyphosphinyl phosphonates (disclosed in U.S. Pat. No. 5,254,544), have the structure

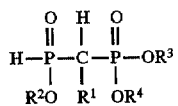

XII and including pharmaceutically acceptable salts thereof, wherein $R^2$, $R^3$ and $R^4$, are independently H, alkyl, a metal ion or a prodrug ester; and $R^1$ is a lipophilic group containing at least 6 carbons, wherein $R^1$ is alkyl, alkenyl, alkynyl or aryl.

$R^1$ can be alkenyl containing from 7 to 25 carbon atoms in the chain and from 1 to 4 double bonds; alkynyl containing 1 to 4 triple bonds; mixed alkenyl-alkynyl containing 1 to 3 double bonds and 1 to 3 triple bonds, and where in the above groups alkyl, alkenyl and/or alkynyl may be substituted or unsubstituted; or a group of the structure

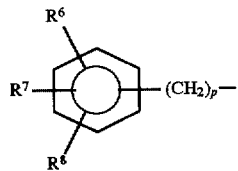

wherein $(CH_2)_p$ contains from 1 to 15 carbons in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, aryl, aryloxy, hydroxy, halogen, nitro, amino, thiol, alkylthio, arylthio, alkylsulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino.

Other squalene synthetase inhibitors suitable for use herein include those disclosed in U.S. Pat. Nos. 5,312,814 and 5,278,153, which are as described below.

U.S. Pat. No. 5,312,814 discloses α-phosphonocarboxylate squalene synthetase inhibitors having the structure

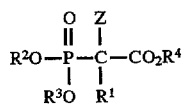

XIII wherein $R^2$ and $R^3$ are independently H, a metal ion, other pharmaceutically acceptable cation, or a prodrug ester;

$R^4$ is H, alkyl, aryl, alkenyl, arylalkyl, metal ion, other pharmaceutically acceptable cation, or a prodrug ester;

$R^1$ is a lipophilic group containing at least 7 carbons and is substituted alkyl, optionally substituted cycloalkyl, optionally substituted cycloalkylalkyl, optionally substituted alkenyl, optionally substituted alkynyl, optionally substituted arylalkyl, or optionally substituted aryl; and Z is H, halogen, lower alkyl, hydroxy or hydroxyalkyl; including pharmaceutically acceptable salts thereof.

U.S. Pat. Nos. 5,278,153 discloses (phosphinylmethyl) phosphonate squalene synthetase inhibitors having the structure

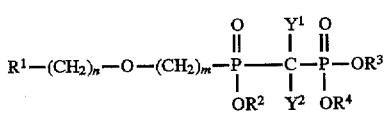

XIV wherein m is 0, 1, 2 or 3; n is 1, 2, 3, 4 or 5;

$Y^1$ and $Y^2$ are H or halogen;

$R^2$, $R^3$ and $R^4$ may be the same or different and are independently H, metal ion, $C_1$ to $C_8$ alkyl, $C_3$ to $C_{12}$ alkenyl, or prodrug ester; and $R^1$ is a substituted or unsubstituted heterocyclic group linked directly or indirectly to $(CH_2)_n$, or a substituted phenyl group, and including all stereoisomers thereof, and wherein $R^1$ can be $R^5$—Q—Y— or $R^5$—Y—Q wherein Y represents a substituted heteroaryl group or a substituted phenyl group;

Q is an alkylene linking group, an alkenylene linking group or an alkynylene linking group or a single bond;

$R^5$ is hydrogen, alkyl, alkenyl or alkynyl and including pharmaceutically acceptable salts thereof.

Other squalene synthetase inhibitors suitable for use herein include (1) Quinuclidine derivatives disclosed in WO 93/13096 (Imperial Chemical Industries) which have the structure

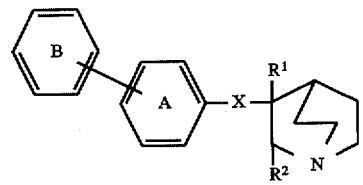

wherein $R^1$ is hydrogen or hydroxy; $R^2$ is hydrogen; or $R^1$ and $R^2$ are joined together so that $CR^1$—$CR^2$ is a double bond; X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —CH=N—, —N=CH—, —$CH_2S$—, —$SCH_2$—, wherein the sulphur atom in the latter two groups may optionally bear one or two oxygen atoms;

and wherein one or both of ring A and ring B may be optionally unsubstituted or independently substituted by one or more substituents selected from halogeno, hydroxy, amino, nitro, cyano, carboxy, carbamoyl, alkyl, alkenyl, alkoxy, alkylamino, di-alkylamino, N-alkylcarbamoyl, N,N-di-alkylcarbamoyl, alkoxycarbonyl, alkylthio, alkylsulphinyl, alkylsulphonyl and halogeno-alkyl;

(2) Cyclic ketal derivatives disclosed in U.S. Pat. No. 5,102,907 to Bergstrom (Merck & Co.) having the structure

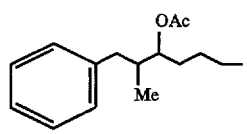

(I)

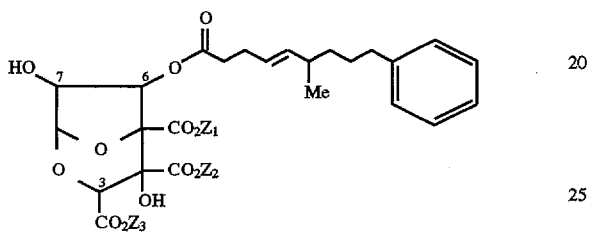

wherein $Z_1$, $Z_2$ and $Z_3$ are each independently selected from:
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt.

(3) Cyclic ketal derivatives disclosed in European Patent Application 0494622A1 (Glaxo) having the structure:

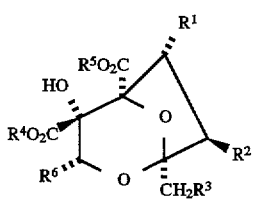

wherein $R^1$ represents a hydrogen atom or a hydroxyl, acyloxy, carbonate, carbamate or ether group;

$R^2$ represents a hydrogen atom, a hydroxyl group, a group —OCOR$^7$ or a group —OCO$_2$R$^7$ (where R$^7$ is a group selected from $C_{1-8}$alkyl, aryl, aryl$C_{1-4}$alkyl and $C_{3-8}$cycloalkyl);

$R^3$ represents a group selected from

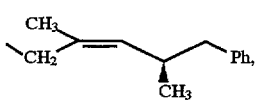

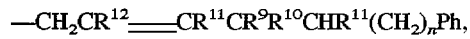

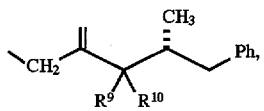

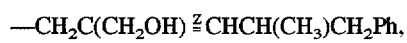
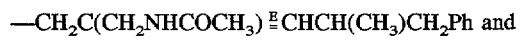

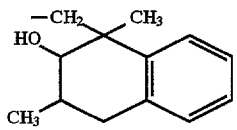

(where the dotted line represents the absence or presence of a single bond, $R^8$ represents a hydrogen atom or a hydroxyl, acyloxy, $C_{1-6}$alkoxy or $C_{1-4}$alkyl group, $R^9$ represents a hydrogen atom and $R^{10}$ represents a hydrogen atom or a hydroxyl, $C_{1-6}$alkoxy or acyloxy group or $CR^9R^{10}$ forms a group C=O, $R^{11}$ represents a hydrogen atom or a $C_{1-4}$alkyl group, $R^{12}$ represents a hydrogen atom or a methyl group, $R^{13}$ represents a hydrogen atom or a hydroxyl group, m represents 1 or 2 and n represents zero or 1);

$R^4$ and $R^5$ may each independently represent a hydrogen atom or a methyl group;

$R^6$ represents a hydrogen atom or a hydroxymethyl group; and salts thereof; with the proviso $R^1$ and $R^2$ cannot both represent hydrogen atoms;

(4) Cyclic ketal derivatives disclosed in European Patent Application 0503520A1 having the structure:

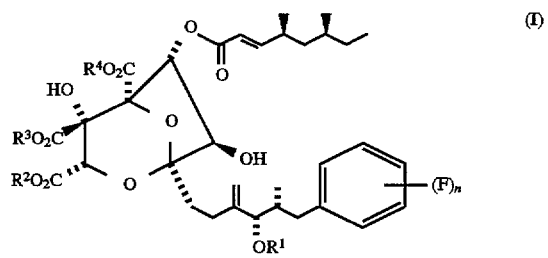

(I)

wherein $R^1$ represents a hydrogen atom or an acetyl group;

$R^2$, $R^3$ and $R^4$ may each independently represent a hydrogen atom or a methyl group; n represents an integer from 1 to 3; and the fluorine atom(s) present may be attached at the ortho, meta or para position of the benzene ring relative to the rest of the molecule; and salts thereof;

(5) Cyclic ketal derivatives disclosed in WO 92/12156 having the structure:

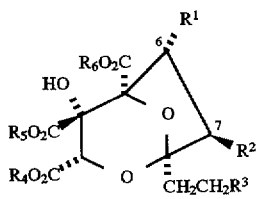

wherein $R_1$ represents a hydrogen atom, a hydroxyl group or a group selected from —OCOCH$\overset{E}{=}$CHCH(CH$_3$)(CH$_2$)$_3$CH$_3$, —OCOCH$\overset{E}{=}$CHC(CH$_3$)$\overset{E}{=}$CHCH(CH$_3$)—CH$_2$CH$_3$, or —OCO—X—CH$_2$CH(CH$_3$)CH$_2$CH$_3$ [where X is —CH$^E$CHCH(CH$_3$)—, —CH$_2$CH(OH)CH(CH$_3$)—, —CH$\overset{E}{=}$CHC(OH)(CH$_3$)—, —CH$_2$CH(OH)CH$_2$— or —CH$_2$CH$_2$CH(CH$_3$)—];

$R_2$ represents a hydrogen atom or a hydroxyl group; $R_3$ represents a group selected from —C(=CH$_2$)CH(OR$_7$)CH(CH$_3$)CH$_2$Ph (where $R_7$ is a hydrogen atom or an acetyl group), —C(CH$_3$)$\overset{E}{=}$CHCH(CH$_2$R$_8$)CH$_2$Ph (where $R_8$ is a hydrogen or a hydroxyl group), —C(CH$_2$OH)$\overset{Z}{=}$CHCH(CH$_3$)CH$_2$Ph, —C(=CH$_2$)CH(OH)CH(CH$_2$OH)CH$_2$Ph,
—C(=CH$_2$)CH(NHCOCH$_3$)CH(CH$_3$)CH$_2$Ph, —C(CH$_2$NHCOCH$_3$)$\overset{E}{=}$CHCH(CH$_3$)CH$_2$Ph or

$R_4$, $R_5$ and $R_6$ may each independently represent a hydrogen atom or a methyl group and salts thereof; with the proviso that when either of $R_1$ and $R_2$ represents a hydrogen atom $R_3$ is a group selected from —C(=CH$_2$)CH(OR$_7$)CH(CH$_3$)CH$_2$Ph and —C(CH$_3$)$\overset{E}{=}$CHCH(CH$_3$)CH$_2$Ph and when both of $R_1$ and $R_2$ represent hydrogen atoms $R_3$ represents —C(CH$_3$)$^E$CHCH(CH$_3$)CH$_2$Ph;

(6) Cyclic ketal derivatives disclosed in WO 92/12157 having the structure:

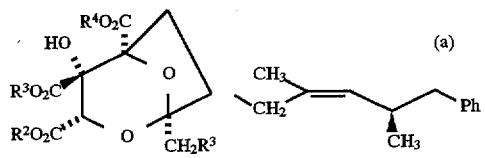

(a)

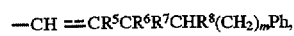 (b)

—CH=CR$^5$CR$^6$R$^7$CHR$^8$(CH$_2$)$_m$Ph, (c)

CH$_2$CR$^9$=CR$^8$CR$^6$R$^7$CHR$^8$(CH$_2$)$_n$Ph,

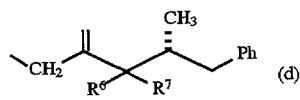 (d)

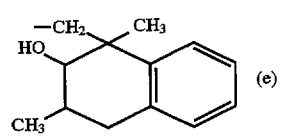 (e)

wherein $R^1$ represents a group selected from (a), (b), (c), (d),

—CH$_2$C(CH$_3$)$\overset{E}{=}$CHCH(CH$_2$OH)CH$_2$Ph,

—CH$_2$C(CH$_2$OH)$\overset{Z}{=}$CHCH(CH$_3$)CH$_2$Ph,

—CH$_2$C(=CH$_2$)CH(OH)CH(CH$_2$OH)CH$_2$Ph,
—CH$_2$C(=CH$_2$)CH(NHCOCH$_3$)CH(CH$_3$)CH$_2$Ph,

—CH$_2$C(CH$_2$NHCOCH$_3$)$\overset{E}{=}$CHCH(CH$_3$)CH$_2$Ph and (e) (where the dotted line represents the absence or presence of a single bond, $R^5$ represents a hydrogen atom or a hydroxyl, acyloxy, $C_{1-6}$alkoxy or $C_{1-4}$alkyl group, $R^6$ represents a hydrogen atom and $R^7$ represents a hydrogen atom or a hydroxyl, $C_{1-6}$alkoxy or acyloxy group or CR$^6$R$^7$ forms a group C=O, $R^8$ represents a hydrogen atom or a $C_{1-4}$alkyl group, $R^9$ represents a hydrogen atom or a methyl group, m represents 1 or 2 and n represents zero or 1); $R^2$, $R^3$ and $R^4$ may each independently represent a hydrogen atom or a methyl group; and salts thereof;

(7) Cyclic ketal derivatives disclosed in WO 92/12158 having the structure:

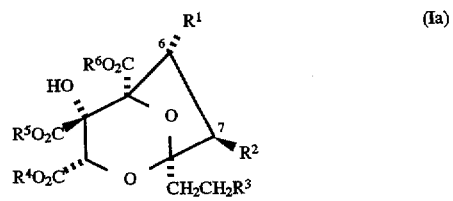 (Ia)

-continued

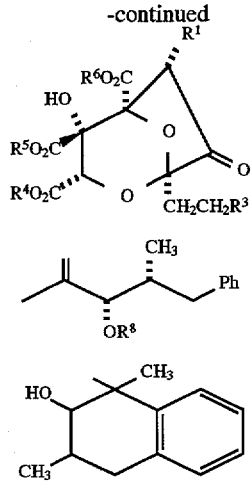

wherein $R^1$ represents a hydrogen atom, a hydroxyl group or a group selected from

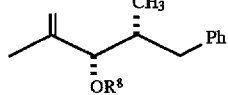

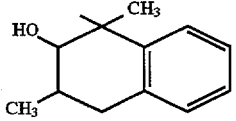

[where X is $-\overset{E}{CH=}CHCH(CH_3)-$, $-CH_2CH(OH)CH(CH_3)-$, $-\overset{E}{CH=}CHC(OH)(CH_3)-$,
$-CH_2CH(OH)CH_2-$ or $-CH_2CH_2CH(CH_3)-$];

$R^2$ represents a hydroxyl group, a group $-OCOR^7$ or a group $-OCO_2R^7$ (where $R^7$ is a group selected from $C_{1-8}$alkyl, aryl, aryl$C_{1-4}$alkyl and $C_{3-8}$cycloalkyl); $R^3$ represents a group selected from (a) (where $R^8$ is a hydrogen atom or an acetyl group),

(where $R^9$ is a hydrogen or a hydroxyl group),

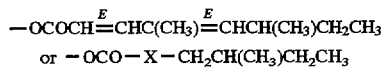

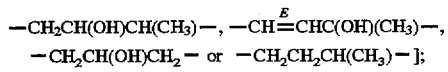

and (b); $R^4$, $R^5$ and $R^6$ may each independently represent a hydrogen atom or a methyl group; and salt thereof;

(8) Cyclic ketal derivatives disclosed in WO 92/12159 having the structure:

wherein $R^1$ represents a hydrogen atom or a hydroxyl, acyloxy, carbonate, carbamate or ether group;
$R^2$ represents a hydrogen atom, a hydroxyl group, a group $-OCOR^7$ or a group $-OCO_2R^7$ (where $R^7$ is a group selected from $C_{1-8}$alkyl, aryl, aryl$C_{1-4}$alkyl and $C_{3-8}$cycloalkyl);

$R^3$ represents a group selected from

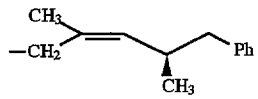

$-CH=CR^8CR^9R^{10}CHR^{11}(CH_2)_mPh$, $-CH_2CR^{12}=CR^{11}CR^9R^{10}CHR^{11}(CH_2)_nPh$,

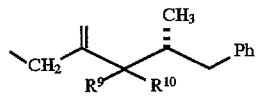

$-CH_2C(CH_3)\overset{E}{=}CHCH(CH_2R^{13})CH_2Ph$, $-CH_2C(CH_2OH)\overset{Z}{=}CHCH(CH_3)CH_2Ph$, $-CH_2C(=CH_2)CH(OH)CH(CH_2OH)CH_2Ph$,
$-CH_2C(=CH_2)CH(NHCOCH_3)CH(CH_3)CH_2Ph$, $-CH_2C(CH_2NHCOCH_3)\overset{E}{=}CHCH(CH_3)CH_2Ph$ and

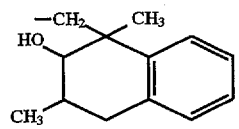

(where the dotted line represents the absence or presence of a single bond, $R^8$ represents a hydrogen atom or a hydroxyl, acyloxy, $C_{1-6}$alkoxy or $C_{1-4}$alkyl group, $R^9$ represents a hydrogen atom and $R^{10}$ represents a hydrogen atom or a hydroxyl, $C_{1-6}$alkoxy or acyloxy group or $CR^9R^{10}$ forms a group $C=O$, $R^{11}$ represents a hydrogen atom or a $C_{1-4}$alkyl group, $R^{12}$ represents a hydrogen atom or a methyl group, $R^{13}$ represents a hydrogen atom or a hydroxyl group, m represents 1 or 2 and n represents zero or 1);

$R^4$, $R^5$ and $R^6$ may each independently represent a hydrogen atom or a methyl group; and salts thereof;

(9) Phosphorus substituted isoprenoid derivatives disclosed in WO 93/04073 having the structure

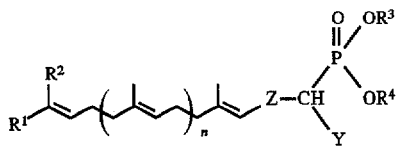

wherein $R_{1,2}$=H, lower alkyl, cycloalkyl, alkenyl, alkynyl, (substituted) aryl, (substituted) arylalkyl, etc. $R_{3-5}$=H, lower alkyl, alkali metal Y=P(O)(OR$_5$)$_2$, $CO_2R_6$  Z=(CH$_2$)$_m$,(CH$_2$)$_p$—CH=CH—(CH$_2$)$_q$, $ANR_6(CH_2)_r$, $R_6$=H, lower alkyl m=0–3 p=0,1 q=1,2 A=$C^{1-5}$alkylene;

(10) 1,1-Bisphosphonic acid compounds disclosed in European Patent Application 0541037A2 having the structure $$\begin{array}{c} P(O)(OR^1)(OR^2) \\ | \\ A-C-B \\ | \\ P(O)(OR^3)(OR^4) \end{array}$$

wherein $R^1$, $R^2$, $R^3$ and $R^4$ is hydrogen or lower alkyl, A is hydrogen, halogen, nitro, an optionally substituted hydrocarbon group, an optionally substituted heterocyclic group, optionally substituted acyl, optionally substituted amino, optionally substituted hydroxy, optionally substituted thiol, Ra—SO—, Ra—SO$_2$—, Ra—CS— (wherein Ra is an optionally substituted hydrocarbon group) or optionally substituted carboxyl, B is hydrogen, halogen, an optionally substituted hydrocarbon group, an optionally substituted heterocyclic group or optionally substituted carboxyl;

(11) Methanediphosphonic acid derivatives disclosed in WO 93/05052 having the structure wherein D=S, O, NH, N-alkyl, CH$_2$, SCH$_2$
X=alkyl which may be substituted by a heteroatom, acyl, aryl
m=1–5
$R_{1-4}$=H, $C_{1-7}$alkyl and the like as disclosed in WO 93/05052;

(12) Polycyclic tertiary amino compounds disclosed in WO 92/15579 having the structure where:
Ar I and Ar II are independently a substituted or unsubstituted mono-, bi- or tricyclic ring;
A is a nitrogen containing heterocycle as disclosed in WO 93/05052;
B is CR'R', O, S, NR', SO, SO$_2$, NR'—C=O, O=C—NR', O=C, R'C=CR' or C≡C;
D is CR'R', O, S, NR', SO, SO$_2$, NR'—C=O, O=C—NR', O=C, O—C=O, O=C—O, O=C—C=O, O=C—CH=CH, R'C=CR', C≡C, C=CHR', C=S, C=NOH or a bond;
$R_1$, $R_2$, $R_3$, $R_4$, $R_5$, $R_6$, $R_7$ and $R_8$ are independently hydrogen or (CH$_2$)$_x$—X where x is 0–5 and X is hydrogen, alkyl, alkenyl, aralkyl, hydroxy, alkoxy, aryloxy, aralkoxy, acyloxy, aryl, halo, amino, mono- and di-alkylamino or acylamino;
$R_1$ and $R_3$, together and/or $R_5$ and $R_7$ together may be (CH$_2$)$_n$ where n is 1–4:

geminal $R_1$ and $R_2$, $R_3$ and $R_4$, $R_5$ and $R_6$ or $R_7$ and $R_8$ groups may be (CH$_2$)$_p$ where p is 2–5;
R' is hydrogen, alkyl or aralkyl;
R is hydrogen, alkyl, aralkyl, hydroxy, alkoxy, aralkoxy, acyloxy, halo, haloalkyl, amino, mono- and di-alkylamino or acylamino; and
a, b, d and e are 0–4; or
a pharmaceutically acceptable salt thereof;

(13) Quinuclidinyl-oxadiazole compounds disclosed in U.S. Pat. No. 5,135,935 having the structure or a pharmaceutically acceptable salt thereof, wherein A and $R^1$ are as described in U.S. Pat. No. 5,135,935;

(14) Biphenylylquinuclidines disclosed in WO 93/09115 having the structure wherein $R^1$ is hydrogen or hydroxy; $R^2$ is hydrogen; or $R^1$ and $R^2$ are joined together so that $CR^1$–$CR^2$ is a double bond; and one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di[(1–6C)alkyl]amino, N-[(1–6C)alkyl]carbamoyl, N,N-di[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl;

(15) 11-Oxo-octadec-3-enoic acid derivatives disclosed in European Patent Application 526936-A2 having the structure wherein R=benzyl, 4-hydroxybenzyl or 3-indolylmethyl;
$Z_1$, $Z_2$ and $Z_3$=H or 1–5C alkyl (optionally substituted by phenyl (optionally substituted by Me, MeO, Cl, Br, I, F or OH));

(16) Bridged cyclic ketal derivatives disclosed in European Patent Application 0494622A having the structure

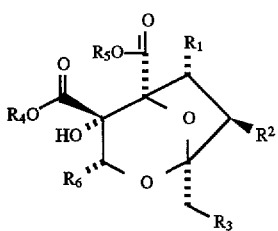

wherein $R_1$=H, OH, acyloxy, etc.;
$R_2$=H, OH, —$OCOR_7$, etc. ($R_7$=Alkyl, aryl and cycloalkyl); $R_3$=Alkenylphenyl, etc.; $R_4$, $R_5$= (Independently) H or $CH_3$; $R_6$=H or hydroxymethyl;

(17) Cyclic ketal derivatives disclosed in WO 92/16530 having the structure

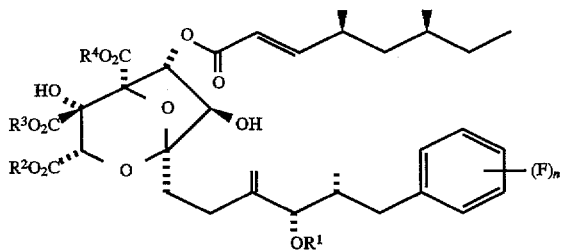

wherein $R^1$ represents a hydrogen atom or an acetyl group; $R^2$, $R^3$ and $R^4$ may each independently represent a hydrogen atom or a methyl group; n represents an integer from 1 to 3; and the fluorine atom(s) present may be attached at the ortho, meta or para position of the benzene ring relative to the rest of the molecule; and salts thereof;

(18) The methylene phosphonoalkylphosphinate esters also referred to as a phosphonomethylphosphinate and/or salt thereof as disclosed in U.S. application Ser. No. 699,049 suitable for use herein are described in European Patent Application 0298553A1 (Norwich Eaton Pharmaceuticals, Inc.), published Jan. 11, 1989, (hereinafter referred to as EP 0298553).

The EP 0298553 compounds useful in the method of the invention are methylene phosphonoakylphosphinic acids, and the pharmaceutically acceptable salts and esters thereof, having the general structure:

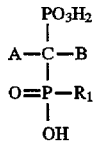   (1)

wherein $R_1$ is selected from hyrogen, substituted alkyl and unsubstituted alkyl. A and B are independently substituent moieties, at least one of which is a lipophilic group.

The term "lipophilic group" is as defined hereinbefore.

The term "alkyl" as used herein, unless otherwise specified, means chemically-stable carbon-containing chains which may be straight, branched, or cyclic; and further which may be saturated, monounsaturated (e.g., one double bond; one triple bond), or polyunsaturated (e.g., two double bonds; two triple bonds; three double bonds; one double and one triple bond). Preferred alkyl have from 1 to about 20 carbon atoms. "Cycloalkyls" as used herein, having from about 3 to about 10 carbon atoms are preferred. Also preferred are straight chain alkyl, saturated alkyl or monounsaturated alkyl.

Alkyl is preferably unsubstituted but may be substituted. Preferred substituent groups for alkyl are as follows: halogen, nitro, cyano, heterocycle, aryl, heteroaryl, unsubstituted amino, and the amide thereof derived from a carboxylic acid of an alkyl, heterocycle, aryl or heteroaryl group, amino substituted with one alkyl, heterocycle, aryl or heteroaryl group and the amide thereof derived from a carboxylic acid of an alkyl group, amino substituted independently with one alkyl group and one alkyl, heterocycle, aryl or heteroaryl group, hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof, —$SO_3H$, the pharmaceutically acceptable salts thereof, the ester thereof derived from an alcohol of an alkyl group, the unsubstituted amide thereof, and the amide thereof substituted with one or two alkyl groups, —$CO_2H$, the pharmaceutically acceptable salts thereof, the ester thereof derived from an alcohol of an alkyl group, the unsubstituted amide thereof, and the amide groups, substituted with one or two alkyl groups, $PO_3H_2$, the pharmaceutically acceptable salts thereof, the ester thereof derived from an alcohol of an alkyl group, the unsubstituted amide thereof, and the amide thereof substituted with one or two alkyl groups, —$(R^8)PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups, aldehyde, ketone having an alkyl group, carbamate, unsubstituted or substituted with one or two alkyl groups, peptidyl, and combinations thereof.

The term "lower alkyl" as used herein, unless otherwise specified, means unsubstituted alkyl having from 1 to about 6 carbon atoms which may be saturated or unsaturated. Preferred lower alkyl are saturated and have from one to about 4 carbon atoms. For lower alkyl groups specified herein as substituted, preferred substituents are the same as for alkyl hereinabove.

The term "heterocycle" as used herein, unless otherwise specified, means chemically-stable nonaromatic rings, including fused non-aromatic rings, having from about 5 to about 20 atoms, comprising at least one heteroatom selected from nitrogen, sulfur, phosphorus and oxygen. Preferred are 5 and 6 membered ring heterocycles which comprise from about 1 to about 3 heteroatoms. More preferred are 5 and 6 membered ring heterocycles which comprise one or two heteroatoms (especially nitrogen heteroatoms). Most preferred are the 6 membered ring heterocycles comprising one nitrogen atom, especially piperidinyl and piperidinylidene heterocycles. Heterocycles may be unsubstituted or substituted, saturated or unsaturated. Preferred heterocycles are unsubstituted or substituted with alkyl; halogen; nitro; cyano; heterocycle; aryl; heteroaryl; unsubstituted amino, and the amide thereof derived from a carboxylic acid of an alkyl heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thio, and the thiol ester thereof derived from a carboxylic acid of an alkyl, heterocycle, aryl or heteroaryl group; thioether having an alkyl, heterocycle, aryl or hetero aryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol of an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof.

The term "aryl", as used herein, unless otherwise specified, mean chemically-stable aromatic rings, including fused aromatic rings, having from about 6 to about 20 carbon atoms. Preferred aryl are phenyl or naphthyl, most preferred is phenyl. Aryls may be unsubstituted or substituted. Preferred aryls are unsubstituted or substituted with alkyl; halogen; nitro; cyano; heterocycle; aryl; heteroaryl, unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol of an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof.

The term "heteroaryl", as used herein, unless otherwise specified, means chemically-stable aromatic rings, including fused aromatic rings and fused aromatic and non-aromatic rings, having from about 30 to about 20 atoms, comprising at least one heteroatom selected from nitrogen, sulfur, phosphorus and oxygen. Preferred are 5 and 6 membered ring heteroaryls which comprise from about 1 to about 3 heteroatoms. More preferred are 5 and 6 membered ring heteroaryls which comprise one or two heteroatoms (especially nitrogen heteroatoms). Most preferred heteroaryl is pyridinyl. Heteroaryls may be unsubstituted or substituted. Preferred heteroaryls are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl heterocyle, aryl or heteroaryl group; hydroxy, and the ester thereof derived from a carboxylic acid of an alkyl heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol or an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof.

The term "substituent group", as used herein, means hydrogen or an alkyl, heterocycle, aryl or heteroaryl group, unless otherwise specified.

$R_1$ is a moiety selected from hydrogen, and alkyl. Preferred $R_1$ is unsubstituted alkyl, especially lower alkyl. Preferred substituents on the $R_1$ alkyl, when substituted, include halogen, alkoxy, unsubstituted and substituted phenyl, hydroxy, carboxy, and chemically-stable combinations thereof.

A is a moiety selected from the group consisting of hydrogen; halogen; nitro; alkyl; heterocycle; aryl; heteroaryl; unsubstituted amino, and the amide thereof derived from a carboxylic acid of a substituent group; amino substituted with one substituent group, and the amide thereof derived from a carboxylic acid of a substituent group; amino substituted independently with one alkyl group and one substituent group; hydroxy, and the ester thereof derived from a carboxylic acid of a substituent group; ether having a substituent group; thiol, and the thiol ester thereof derived from a carboxylic acid of a substituent group; thioether having a substituent group, and the sulfoxide and sulfone derivative thereof; —$SO_3H$, the pharmaceutically acceptable salts thereof, the ester thereof derived from an alcohol of a substituent group, the unsubstituted amide thereof, and the amide thereof substituted with one or two alkyl groups; —$CO_2H$, the pharmaceutically acceptable salts thereof, the ester thereof derived from an alcohol of a substituent group, the unsubstituted amide thereof, and the amide thereof substituted with one or two alkyl groups; aldehyde; ketone having a substituent group; carbamate, unsubstituted or substituted with one or two alkyl groups; pepetides having from about one to about 100 amino acid moieties; or the A and B moieties are covalently linked to form a ring having from 3 to about 7 atoms with from 0 to about 3 heteroatoms selected from the group consisting of nitrogen, sulfur, phosphorus and oxygen, the ring being unsubstituted or substituted with one or more of the above substituents of A; or the A and B moieties are replaced by an unsubstituted or substituted alkyl moiety attached to the geminal carbon by a double bond.

Examples of A moieties include
(1) hydrogen;
(2) halogen; more preferred are F or Cl;
(3) substituted and unsubstituted alkyl having the general structure:

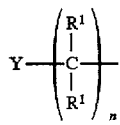 (2)

wherein n is an integer from 1 to about 10, preferably from 1 to about 5, more preferably n=1 or 2, and most preferably n=1; each R1 is independently selected to achieve chemically-stable moieties from the group consisting of hydrogen, halogen, lower alkyl, unsubstituted amino or the amido thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or the pharmaceutically acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically acceptable salts thereof, and nitro, or two $R^1$'s on the same carbon atom are =O or =$NR^9$ (where R9 is lower alkyl or may be hydrogen when there is another nitrogen atom attached to the same carbon atom as the =$NR^9$ moiety), or two $R^1$'s on adjacent carbon atoms may be replaced by an additional bond between the carbon atoms; or an on the first carbon atom (from the right side of structure (2) hereinabove) and B (see structure (1) hereinabove) may be replaced by an additional bond; and Y is a substituent of alkyl as defined hereinbefore; (for the sake of chemical stability of the compounds used in the present invention, $R^1$ cannot be such that there is a halogen and an oxygen or sulfur or nitrogen singly bonded to the same carbon atom or such that two of an oxygen or sulfur or nitrogen are singly bonded to the same carbon atom);
(4) Cycloalkyl having from about 4 to about 10 carbon atoms; more preferred are cycloalkyl having 5 or 6 carbon atoms;
(5) Heterocycle having 5 or 6 atoms in the ring; more preferred are heterocycles having one or two nitrogen atoms in the ring, more preferred still are heterocycles having one nitrogen atom in the ring; most preferred are unsubstituted or substituted piperidinyl, pyrrolidinyl, piperazinyl, morpholinyl;

(6) unsubstituted and substituted phenyl; naphthyl;
(7) Unsubstituted and substituted 5 and 6 membered ring heteroaryls having one or two heteroatoms (especially nitrogen heteroatoms); most preferred is pyridinyl;
(8) amine-containing moiety having the general structure:

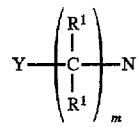

wherein m is an integer from 0 to about 10, preferably from out 5, more preferably 0 or 1, and most preferably m=0; R1 and Y are as described hereinbefore; and $R^2$ is hydrogen, lower alkyl or acyl derived from a carboxylic acid of a lower alkyl;
(9) oxygen-containing moiety having the general structure:

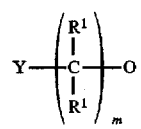

wherein m is an integer from 0 to about 10, preferably from 0 to about 5, more preferably 0 or 1, and most preferably m=0; and $R^1$ and Y are as described hereinbefore; and
(10) sulfur-containing moiety having the general structure:

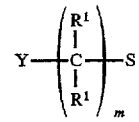

wherein m is an integer from 0 to about 10, preferably from 0 to about 5, more preferably 0 or 1, and most preferably m=0; and R1 and Y are as described hereinbefore;
(11) peptide-containing moiety having the general structure:

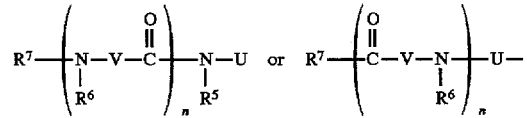

wherein n is an integer from 1 to about 100, preferably from 1 to about 6; $R^5$, each $R^6$ and $R^7$ are independently hydrogen or lower alkyl, preferably $R^5$, each $R^6$ and $R^7$ are hydrogen; U and each V are independently unsubstituted or substituted lower alkyl (substituted such that moiety is chemically-stable), or $R^5$ and U or each $R^6$ and V, together with the included nitrogen atom to which they are bound, may form a five- or six-membered ring which is unsubstituted or substituted; or U may be nil; preferably U and each V or rings in which they are incorporated are moieties found in naturally-occurring amino acid moieties, i.e., lysine, leucine, isoleucine, valine, phenylalanine, arginine, histidine, methionine, alanine, aspartic acid, threonine, proline, glycine, serine, tyrosine, tryptophan, glutamine and cysteine.

Preferred A moieties of the present invention are optionally substituted alkyl, optionally substituted alkenyl, and optionally substituted aryl.

B is a moiety selected from hydrogen; halogen; unsubstituted and substituted lower alkyl; unsubstituted and substituted cycloalkyl having from about 3 to about 7 atoms in the ring; unsubstituted and substituted heterocycle having from about 3 to about 7 atoms in the ring; unsubstituted and substituted phenyl; hydroxy, and the ester thereof derived from a carboxylic acid of a lower alkyl group; thiol; unsubstituted amino, and the amide thereof derived from a carboxylic acid of a lower alkyl group; amino substituted with one lower alkyl group, and the amide thereof derived from a carboxylic acid of a lower alkyl group; amino substituted independently with two lower alkyl groups; —$CO_2H$, the pharmaceutically acceptable salts thereof, the ester thereof derived from an alcohol of a lower alkyl group, the unsubstituted amide thereof, and the amide thereof substituted with one or two lower alkyl groups.

For the sake of chemical stability for the compounds of the present invention, it is preferred that the A and B moieties do not both have heteroatoms (N, O or S), or a heteroatom and a halogen, bonded to the methylene phosphonoalkylphosphinate moiety (i.e., the carbon atom geminally substituted with the phosphorus atoms). Thus, when the A moiety has an oxygen, sulfur, nitrogen, or halogen atom bonded to the phosphorus-substituted methylene carbon, then B is selected from hydrogen; unsubstituted or substituted lower alkyl, cycloalkyl, heterocycle (where a carbon atom of the heterocycle is bonded to the geminal carbon atoms), or phenyl; —$CO_2H$, the pharmaceutically acceptable salts thereof, the ester thereof derived from an alcohol of a lower alkyl group, the unsubstituted amide thereof, and the amide thereof substituted with one or two lower alkyl groups.

Preferred B is selected from hydrogen, halogen, unsubstituted and substituted lower alkyl, unsubstituted and substituted phenyl, unsubstituted and substituted benzyl, hydroxy and the ester thereof derived from a carboxylic acid of a lower alkyl group, thiol, unsubstituted amino and the amide thereof derived from a carboxylic acid of a lower alkyl group, amino substituted with one lower alkyl group and the amide thereof derived from a carboxylic acid of a lower alkyl group, amino substituted independently with two lower alkyl groups, and —$CO_2H$, and the pharmaceutically acceptable salts thereof and the ester thereof derived from an alcohol of a lower alkyl group and the unsubstituted amide thereof or the amide thereof substituted with one or two lower alkyl groups.

In addition, other compounds suitable for use in the method of the invention are disclosed in European Patent Application 0448393A1, European Patent Application 0475706A1, WO 92/22660, European Patent Application 524671A1, European Patent Application 0522715A1, European Patent Application 0512865A2, WO92/12160, U.S. Pat. No. 5,053,425, European Patent Application 0526936A, U.S. Pat. No. 5,026,554, European Patent Application 0524677A1, European Patent 0503520A, GB 2261373A, European Patent Application 93/0541037A2, Application WO 92/15579.

The disclosures of the above U.S. patents and U.S. patent applications and U.S. counterparts to the above mentioned foreign patents and applications are incorporated herein by reference. The preferred compounds in these patents and patent applications are the preferred compounds for use in the method of the invention.

In carrying out the method of the invention, a pharmaceutical composition will be employed containing at least one squalene synthetase inhibitor in association with a pharmaceutical vehicle or diluent. The pharmaceutical composition can be formulated employing conventional solid or liquid vehicles or diluents and pharma-ceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains squalene synthetase inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of sterile squalene synthetase inhibitor into a vial, aseptically freeze-drying and sealing. For use, the contents of the vial are mixed with 2 mL of physiological saline, to produce an injectable preparation.

What is claimed is:

1. A method for inhibiting and/or treating hypertriglyceridemia, which comprises administering to a mammalian species in need of treatment a therapeutically effective amount of a squalene synthetase inhibitor including a prodrug ester thereof, which is exclusive of boron or boron containing moieties, and which inhibits de novo cholesterol biosynthesis.

2. The method as defined in claim 1, wherein the squalene synthetase inhibitor is a bisphosphonate, methylene phosphonoalkyl phophinate, (phosphinylmethyl) phosphonate, α-phosphonocarboxylate, hydroxyphosphinylphosphonate or a phosphinylformic acid including prodrug esters thereof.

3. The method as defined in claim 1, wherein the squalene synthetase inhibitor has the structure

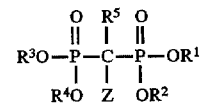

wherein $R^1$, $R^2$, $R^3$ and $R^4$ are the same or different and are H, lower alkyl, a metal ion or a prodrug ester;

$R^5$ is H, halogen or lower alkyl;

Z is substituted alkenyl wherein the alkenyl group contains at least 7 carbon atoms in the chain and from 1 to 4 double bonds; substituted alkynyl containing 1 to 4 triple bonds; mixed alkenyl-alkynyl containing 1 to 3 double bonds and 1 to 3 triple bonds, and wherein alkenyl and/or alkynyl may be substituted or unsubstituted; or a substituted phenylalkyl group of the structure

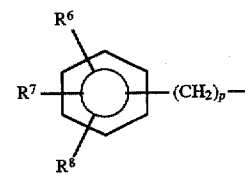

wherein $(CH_2)_p$ contains from 1 to 15 carbons in the chain and may include 0, 1, 2 or 3 double bonds and/or 0, 1, 2 or 3 triple bonds in the normal chain and/or may include 0, 1, 2 or 3 substituents which are alkyl, alkenyl, alkoxy, alkynyl, hydroxy and/or halogen; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino, at least one of $R^6$, $R^7$ and $R^8$ being alkenyl alkenyloxy alkynyl or alkynyloxy, and wherein the total number of carbons in

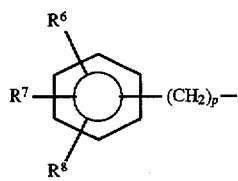

exceeds 10 carbons.

4. The method as defined in claim 3 wherein Z is substituted alkenyl or substituted alkynyl.

5. The method as defined in claim 2, wherein the squalene synthetase inhibitor has the structure

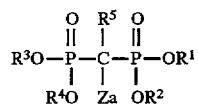

wherein $R^1$, $R^2$, $R^3$ and $R^4$ are the same or different and are H, alkyl, a metal ion or a prodrug ester; $R^5$ is H, halogen or alkyl, and Za is substituted alkenyl which includes 1 to 4 double bonds and is substituted with from 1 to 4 lower alkyl groups.

6. The method as defined claim 2, wherein the squalene synthetase inhibitor has the structure

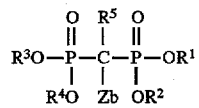

wherein zb is

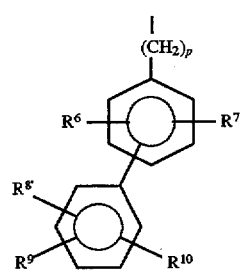

$R^1$, $R^2$, $R^3$ and $R^4$ are the same or different and are H, alkyl, a metal ion or a prodrug ester;

$R^5$ is H, halogen or alkyl;

p is 1 to 15;

$(CH_2)_p$ may include 0, 1, 2 or 3 double bonds and/or 0, 1, 2 or 3 triple bonds in the normal chain, and/or may include 0, 1, 2 or 3 substituents which are alkyl, alkoxy, alkenyl, alkynyl, hydroxy and/or halogen; and $R^6$, $R^7$, $R^8$, $R^9$ and $R^{10}$ are the same or different and are H, alkyl containing 1 to 40 carbons, alkoxy containing 1 to 40 carbons, alkenyl containing 2 to 40 carbons, alkenyloxy containing 2 to 40 carbons, hydroxy, alkynyl containing 2 to 40 carbons, alkynyloxy containing 2 to 40 carbons, aryloxy, halogen, nitro, amino, thio, alkylthio, arylthio, arylsulfinyl, alkylsulfinyl, arylsulfonyl, alkylsulfonyl, carboxy, alkylcarbonyloxy, arylcarbonyloxy, alkoxycarbonyl, aminocarbonyl, arylcarbonylamino or alkylcarbonylamino.

7. The method as defined in claim 2, wherein the squalene synthetase inhibitor has the structure

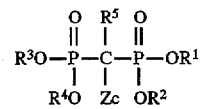

wherein Zc is substituted alkyl containing from 9 to 14 carbons in the normal chain and is substituted with 1 to 4 lower alkyl groups;

$R^1$, $R^2$, $R^3$ and $R^4$ are the same or different and are H, alkyl, a metal ion or a prodrug ester; and $R^5$ is H, halogen or alkyl.

8. The method as defined in claim 2, wherein the squalene synthetase inhibitor has the structure

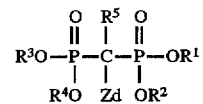

wherein Zd is

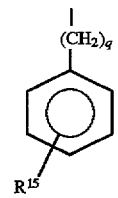

q is 2 to 15, $(CH_2)_q$ may include 0, 1, 2 or 3 double bonds and/or 0, 1, 2 or 3 triple bonds in the normal chain and may optionally include one or more alkyl, alkenyl, alkynyl, hydroxy, alkoxy and/or halogen substituents;

$R^1$, $R^2$, $R^3$ and $R^4$ are the same or different and are H, alkyl, a metal ion or a prodrug ester; and $R^5$ is H, halogen or lower alkyl; and $R^{15}$ is alkyl containing from 2 to 20 carbons;

the total number of carbons in Zd exceeds 10.

9. The method as defined in claim 2, wherein the squalene synthetase inhibitor has the structure

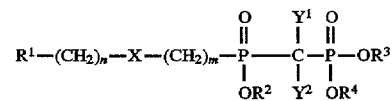

wherein m is 0, 1, 2 or 3; n is 0, 1, 2, 3 or 4;

$Y^1$ and $Y^2$ are H or halogen;

$R^2$, $R^3$ and $R^4$ may be the same or different and are independently H, metal ion, $C_1$ to $C_8$ alkyl or $C_3$ to $C_{12}$ alkenyl;

X is O, S, NH or —NCH$_2$R$^{15}$ wherein R$^{15}$ is H or C$_1$ to C$_5$ alkyl; and R$^1$ is R$^5$—Q$^1$—Q$^2$—Q$^3$— wherein Q$^1$, Q$^2$ and Q$^3$ are the same or different and are independently

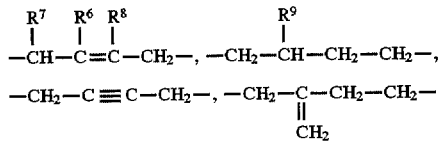

or a single bond, with the proviso that if Q$^1$ is a bond, then Q$^2$ and Q$^3$ are bonds, and if Q$^2$ is a bond then Q$^3$ is a bond, and wherein R$^6$ is H, lower alkyl, halo or haloalkyl; R$^7$ is H, halogen, lower alkyl or lower alkylthio; R$^8$ is H, halogen, trimethylsilyl or lower alkyl; and R$^9$ is H or lower alkyl; R$^5$ is

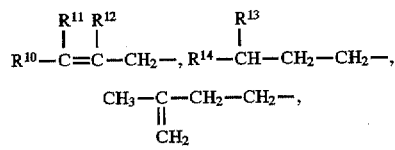

CH$_3$(CH$_2$)$_p$ where p is an integer from 2 to 7, or R$^{16}$—C≡C—CH$_2$— where R$^{16}$ is H or lower alkyl; R$^{10}$, and R$^{11}$ are the same or different and are independently H, lower alkyl, haloalkyl, halogen or lower alkenyl or R$^{10}$ and R$^{11}$ can be taken together to form (CH$_2$)$_s$ where s is an integer from 2 to 7; R$^{12}$ is H, lower alkyl, halogen or lower alkenyl; and R$^{13}$ and R$^{14}$ are the same or different and are independently lower alkyl; with the proviso that if all of Q$^1$, Q$^2$ and Q$^3$ are bonds, then R$^{10}$ and R$^{11}$ cannot both be H, and R$^5$ cannot be CH$_3$(CH$_2$)$_p$ with p less than or equal to 4, and when m is 0, X is other than S; and if m is o and X is O, then n is 1, 2, 3 or 4; and including all stereoisomers thereof.

10. The method as defined in claim 2 wherein the squalene synthetase inhibitor has the structure

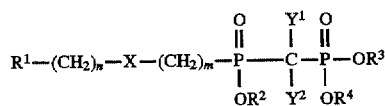

wherein m is 1, 2 or 3; n is 0, 1, 2, 3 or 4;

Y$^1$ and Y$^2$ are H or halogen;

R$^2$, R$^3$ and R$^4$ may be the same or different and are independently H, metal ion, C$_1$ to C$_8$ alkyl or C$_3$ to C$_{12}$ alkenyl;

X is O, S, NH or —NCH$_2$R$^{15}$ wherein R$^{15}$ is H or C$_1$ to C$_5$ alkyl; and R$^1$ is R$^5$—Q$^1$—Q$^2$—Q$^3$— wherein Q$^1$, Q$^2$ and Q$^3$ are the same or different and are independently

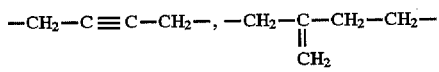

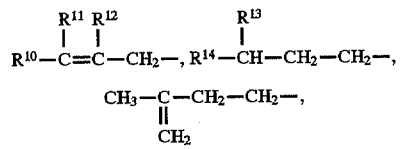

or a single bond, with the proviso that if Q$^1$ is a bond, then Q$^2$ and Q$^3$ are bonds, and if Q$^2$ is a bond then Q$^3$ is a bond, and wherein R$^6$ is H, lower alkyl, halo or haloalkyl; R$^7$ is H, halogen, lower alkyl or lower alkylthio; R$^8$ is H, halogen, trimethylsilyl or lower alkyl; and R$^9$ is H or lower alkyl; R$^5$ is

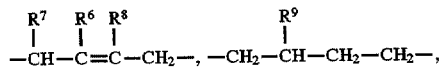

CH$_3$(CH$_2$) where p is an integer from 2 to 7, or R$^{16}$—C≡C—CH$_2$— where R$^{16}$ is H or lower alkyl; R$^{10}$, and R$^{11}$ are the same or different and are independently H, lower alkyl, haloalkyl, halogen or lower alkenyl or R$^{10}$ and R$^{11}$ can be taken together to form (CH$_2$)$_s$ where s is an integer from 2 to 7; R is H, lower alkyl, halogen or lower alkenyl; and R$^{13}$ and R$^{14}$ are the same or different and are independently lower alkyl; with the proviso that if all of Q$^1$, Q$^2$ and Q$^3$ are bonds, then both R$^{10}$ and R$^{11}$ cannot be H, and R$^5$ cannot be CH$_3$(CH$_2$)$_p$ with a p less than or equal to 4, and including all stereoisomers thereof.

11. The method as defined in claim 2 wherein the squalene synthetase inhibitor has the structure

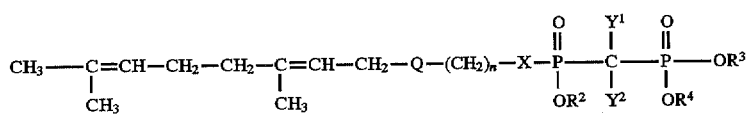

wherein Q is

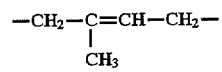

or a bond;

n is 0 to 4;

X is O, —NH— or NCH$_2$R$^{15}$;

R$^2$, R$^3$ and R$^4$ are the same or different and are H, lower alkyl, lower alkenyl, or a metal ion;

Y$^1$ and Y$^2$ may be the same or different and are H or halogen; and

R$^{15}$ is H or lower alkyl;

with the proviso that when X is O, n is 1, 2, 3, or 4.

12. The method as defined in claim 2 wherein the squalene synthetase inhibitor has the structure

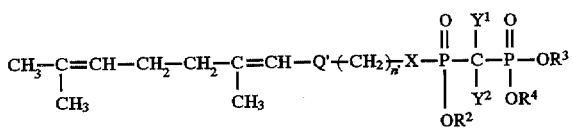

wherein Q' is

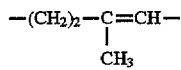

or a bond;

n' is 1, 2, 3 or 4;

X is O, —NH— or NCH$_2$R$^{15}$,

R$^2$, R$^3$ and R$^4$ are the same or different and are H, lower alkyl, lower alkenyl, or a metal ion;

Y$^1$ and Y$^2$ may be the same or different and are H or halogen; and

R$^{15}$ is H or lower alkyl;

with the proviso that when X is O, n' is 2, 3, or 4.

13. The method as defined in claim 2 wherein the squalene synthetase inhibitor has the structure

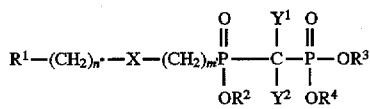

wherein m' is 1, 2 or 3; n" is 0, 1, 2 or 3;

Y$^1$ and Y$^2$ are H or halogen;

R$^2$, R$^3$ and R$^4$ may be the same or different and are independently H, metal ion, C$_1$ to C$_8$ alkyl or C$_3$ to C$_{12}$ alkenyl;

X is O, S, NH or —NCH$_2$R$^{15}$ wherein R$^{15}$ is H or C$_1$ to C$_5$ alkyl; and R$^1$ is R$^5$—Q$^1$—Q$^2$—Q$^3$— wherein Q$^1$, Q$^2$ and Q$^3$ are the same or different and are independently

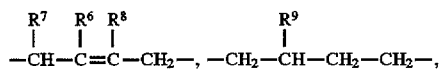

—CH$_2$—C≡C—CH$_2$—, or a single bond, with the proviso that if Q$^1$ is a bond, then Q$^2$ and Q$^3$ are bonds, and if Q$^2$ is a bond then Q$^3$ is a bond, and wherein R$^6$ is H, lower alkyl, halo or haloalkyl; R$^7$ is H, halogen, lower alkyl or lower alkylthio; R$^8$ is H, halogen, trimethylsilyl or lower alkyl; and R$^9$ is H or lower alkyl; R$^5$ is

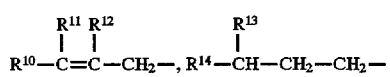

CH$_3$(CH$_2$)$_p$ where p is an integer from 2 to 7, or R$^{16}$—C≡C—CH$_2$— where R$^{16}$ is H or lower alkyl; R$^{10}$, and R$^{11}$ are the same or different and are independently H, lower alkyl, haloalkyl, halogen or lower alkenyl or R$^{10}$ and R$^{11}$ can be taken together to form (CH$_2$)$_s$ where s is an integer from 2 to 7; is H, lower alkyl, halogen or lower alkenyl; and R$^{13}$ and R$^{14}$ are the same or different and are independently lower alkyl; with the proviso that if all of Q$^1$, Q$^2$ and Q$^3$ are bonds, then both R$^{10}$ and R$^{11}$ cannot be H, and R$^5$ cannot be CH$_3$(CH$_2$)$_p$ with a p less than or equal to 4, and including all stereoisomers thereof.

14. The method as defined in claim 1 wherein the squalene synthetase inhibitor has the formula

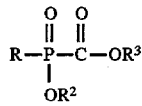

wherein R$^2$ is a metal ion, lower alkyl or H; R$^3$ is a metal ion or lower alkyl; R is R$^1$—(CH$_2$)$_n$—, R$^1$—(CH$_2$)$_m$O— or R$^1$—(CH$_2$)$_m$OCH$_2$—, wherein n is an integer from 1 to 4 and m is an integer from 0 to 3; and R$^1$ is R$^5$—Q$^1$—Q$^2$—Q$^3$— wherein Q$^1$, Q$^2$ and Q$^3$ are independently:

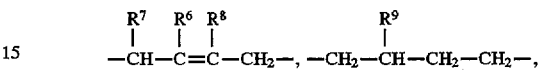

—CH$_2$—C≡C—CH$_2$—, or a bond, with the stipulation that if Q$^1$ is a bond, then Q$^2$ and Q$^3$ must be bonds, and if Q$^2$ is a bond, then Q$^3$ is a bond; R$^6$ is H, lower alkyl, fluoro or fluoroalkyl; R$^7$ is H, fluoro, lower alkyl or alkylthio; R$^8$ is H, fluoro, trimethylsilyl or lower alkyl; R$^9$ is H, or lower alkyl; R$^5$ is

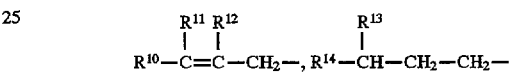

R$^{16}$—C≡C—CH$_2$— (wherein R$^{16}$ is lower alkyl or H), or CH$_3$(CH$_2$)$_p$— where p is 2 to 7; R$^{10}$ and R$^{11}$ are independently hydrogen, lower alkyl, fluoro, lower alkenyl or fluoroalkyl or R$^{10}$ and R$^{11}$ can be taken together to form (CH$_2$)$_s$, where s is 2 to 7; R$^{12}$ is hydrogen, lower alkyl, fluoro or lower alkenyl; R$^{13}$ and R$^{14}$ are independently lower alkyl; with the proviso that if all of Q$^1$, Q$^2$ and Q$^3$ are bonds, then R$^{10}$ and R$^{11}$ cannot both be H, and R$^5$ cannot be CH$_3$(CH$_2$)$_p$, with p≦4, including all stereoisomers thereof.

15. The method as defined in claim 1 wherein the squalene synthetase inhibitor has the structure

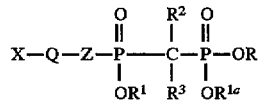

wherein Q is

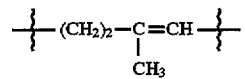

or a bond;

Z is —(CH$_2$)$_n$— or —(CH$_2$)$_p$—CH=CH—(CH$_2$)$_m$—, wherein n is 1 to 5; p is 0, 1 or 2; m is 0, 1 or 2;

R, R$^1$ and R$^{1a}$ are the same or different and are H, lower alkyl or a metal ion;

R$^2$ and R$^3$ may be the same or different and are H or halogen; and X is

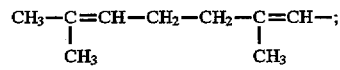

or the squalene synthetase inhibitor has the structure

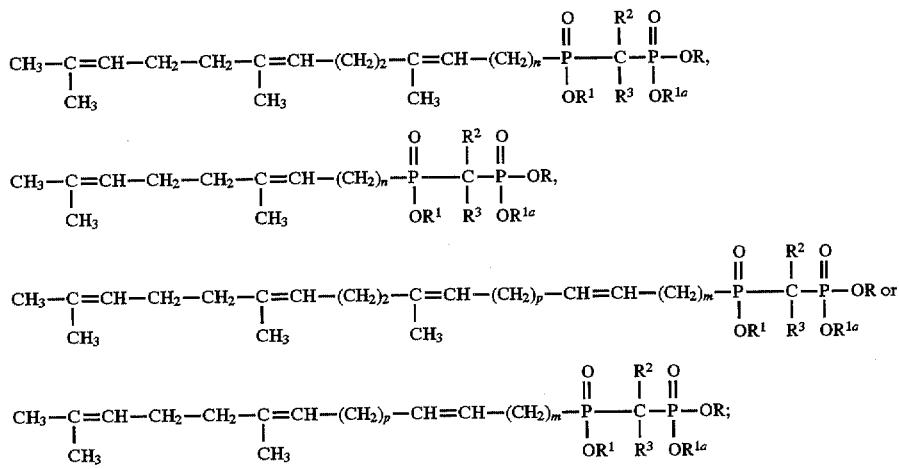

or the squalene synthetase inhibitor has the structure

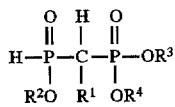

wherein $R^2$, $R^3$ and $R^4$, are independently H, alkyl, a metal ion or a prodrug ester; and $R^1$ is a lipophilic group containing at least carbons, and including pharmaceutically acceptable salts thereof.

16. A method for inhibiting or treating atherosclerosis and/or pancreatitis resulting from hypertriglyceridemia, which comprises administering to a mammalian species in need of treatment a therapeutically effective amount of a squalene synthetase inhibitor, including a prodrug ester thereof, which is free of boron or boron containing moieties, and which inhibits de novo cholesterol biosynthesis.

17. The method as defined in claim 16, wherein the squalene synthetase inhibitor is a bisphosphonate, (phosphinylmethyl)phosphonate, α-phosphonocarboxylate, hydroxyphosphinylphosphonate, methylene phosphonoalkyl phosphinate, or a phosphinylformic acid including prodrug esters thereof.

18. A method for inhibiting and/or treating hypertriglyceridemia or atherosclerosis and/or pancreatitis resulting from hypertriglyceridemia, which comprises administering to a mammalian species in need of treatment a therapeutically effective amount of a phosphorus-containing squalene synthetase inhibitor including a prodrug ester thereof which is free of boron or boron containing moieties, and which inhibits de novo cholesterol biosynthesis.

* * * * *

UNITED STATES PATENT AND TRADEMARK OFFICE
CERTIFICATE OF CORRECTION

PATENT NO. : 5,712,261
DATED : Jan. 27, 1998
INVENTOR(S) : David R. Magnin et al It is certified that error appears in the above-identified patent and that said Letters Patent is hereby corrected as shown below:

In Column 28, line 21, please change "$CH_3(CH_2)$" to --$CH_3(CH_2)_p$-- ;

In Column 30, line 38, please change "$p \leq 4$" to --$p \leq 4$--;

In Column 31, line 31, please insert --6-- after "at least" and before " carbons".

Signed and Sealed this

Sixth Day of October, 1998

Attest:

BRUCE LEHMAN

*Attesting Officer*  *Commissioner of Patents and Trademarks*